US008404149B2

(12) United States Patent
Stegmann et al.

(10) Patent No.: US 8,404,149 B2
(45) Date of Patent: Mar. 26, 2013

(54) ABSORBENT ARTICLE COMPRISING WATER-ABSORBING MATERIAL

(75) Inventors: Veit Stegmann, Mannheim (DE); Klemens Massonne, Bad Dürkheim (DE); Franz Niklaus Windlin, Heidelberg (DE); Reinhold Schwalm, Wachenheim (DE); Dieter Hermeling, Böhl-Iggelheim (DE); Thomas Daniel, Waldsee (DE); Stefan Bruhns, Mannheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 853 days.

(21) Appl. No.: 12/557,593

(22) Filed: Sep. 11, 2009

(65) Prior Publication Data

US 2010/0108944 A1 May 6, 2010

(30) Foreign Application Priority Data

Sep. 12, 2008 (EP) .................................. EP08164242

(51) Int. Cl.
*B01J 20/04* (2006.01)
*B01J 20/16* (2006.01)
*B01J 20/18* (2006.01)
*C09K 3/00* (2006.01)
*C08K 3/08* (2006.01)
*C08K 3/10* (2006.01)

(52) U.S. Cl. ........ 252/194; 524/403; 524/407; 524/413; 524/431; 524/558; 427/508

(58) Field of Classification Search .................. 252/194; 524/403, 407, 413, 431, 558; 427/508
See application file for complete search history.

(56) References Cited

U.S. PATENT DOCUMENTS

| 5,398,434 | A | 3/1995 | Biancalani |
| 5,948,829 | A | 9/1999 | Wallajapet et al. |
| 6,831,122 | B2 * | 12/2004 | Daniel et al. ................... 524/417 |
| 7,285,615 | B2 * | 10/2007 | Adachi et al. ................... 526/319 |
| 2004/0048955 | A1 * | 3/2004 | Wada et al. ......................... 524/9 |
| 2004/0077796 | A1 * | 4/2004 | Daniel et al. ................... 525/360 |
| 2005/0049379 | A1 | 3/2005 | Adachi et al. |
| 2005/0209352 | A1 * | 9/2005 | Dairoku et al. ................... 521/50 |
| 2006/0128827 | A1 | 6/2006 | Matsumoto et al. |
| 2007/0149691 | A1 * | 6/2007 | Ishizaki et al. ................. 524/500 |
| 2008/0032888 | A1 | 2/2008 | Nakamura et al. |
| 2008/0269372 | A1 * | 10/2008 | Dairoku et al. ............... 523/149 |
| 2009/0270538 | A1 * | 10/2009 | Ikeuchi et al. ................. 524/115 |
| 2011/0046279 | A9 * | 2/2011 | Ikeuchi et al. ................. 524/115 |
| 2011/0275513 | A1 * | 11/2011 | Tian et al. ....................... 502/402 |

FOREIGN PATENT DOCUMENTS

WO WO 2007/141875 12/2007

OTHER PUBLICATIONS

PCT International Search Report, PCT/US2009/056426 dated Oct. 9, 2009.

* cited by examiner

*Primary Examiner* — Joseph D Anthony
(74) *Attorney, Agent, or Firm* — Andrew A Paul; Richard L. Alexander

(57) ABSTRACT

The present disclosure relates to an absorbent structure for use in a diaper for babies and infants, a feminine hygiene article and/or an incontinence article, said absorbent structure comprising a water-absorbing material, the water-absorbing material being obtainable by a process comprising the steps of A) treating a particulate, non-surface-crosslinked, water-absorbing polymer with a mixture comprising an aqueous solvent and at least one salt of a transition metal and B) irradiating the polymer treated according to A) with UV radiation, and to a process for its production.

11 Claims, No Drawings

ABSORBENT ARTICLE COMPRISING WATER-ABSORBING MATERIAL

CROSS REFERENCE TO RELATED APPLICATION

This application claims priority to EPO Patent Application 08164242.3, filed Sep. 12, 2008, the substance of which is incorporated herein by reference.

FIELD OF THE INVENTION

This disclosure relates to improved absorbent structures comprising a water-absorbing material, and to a process for its production and to its use.

BACKGROUND OF THE INVENTION

An important component of disposable absorbent articles such as diapers is an absorbent core structure comprising water-absorbing polymeric particles, typically hydrogel-forming water-swellable polymers, also referred to as absorbent gelling material, AGM, or super-absorbent polymers, or SAP's. This polymer material ensures that large amounts of bodily fluids, e.g. urine, can be absorbed by the article during its use and locked away, thus providing low rewet and good skin dryness.

Water-absorbing polymers are known. For such materials, names such as "highly swellable polymer" "hydrogel" (often also used for the dry form), "hydrogel-forming polymer", "superabsorbent polymer", "superabsorbent", "absorbent gel-forming material", "swellable resin", "water-absorbing resin" or the like are also common. These polymers are crosslinked hydrophilic polymers, especially polymers formed from (co)polymerized hydrophilic monomers, graft (co)polymers of one or more hydrophilic monomers on a suitable graft base, crosslinked cellulose ethers or starch ethers, crosslinked carboxymethylcellulose, partly crosslinked polyalkylene oxide or natural products swellable in aqueous liquids, for example guar derivatives, water-absorbing polymers based on partly neutralized acrylic acid being the most widespread. The essential properties of water-absorbing polymers are their ability to absorb several times their own weight of aqueous liquids and not to release the liquid again, even under a certain pressure. The water-absorbing polymer, which is used in the form of a dry powder, is converted to a gel when it absorbs liquid and correspondingly to a hydrogel when it absorbs water, as is customary. By far the most important field of use of water-absorbing polymers is the absorption of body fluids. Water-absorbing polymers are used, for example, in diapers for infants, incontinence products for adults or feminine hygiene products. Other fields of use are, for example, those as water-retaining agents in market gardening, as a water store for protection from fire, for liquid absorption in food packaging or quite generally for absorption of moisture.

While many treatments of these materials are known, it has been found that these treatments do not lead to surface-modified polymers having the desired absorption properties. Furthermore, there is a need to deliver a process having a good space-time yield.

SUMMARY OF THE INVENTION

An absorbent structure for use in diapers for babies and infants, feminine hygiene articles and/or incontinence articles has been found, wherein the absorbent structure comprises comprising a water-absorbing material obtained by a process comprising the steps of:
A) treating a particulate, non-surface-crosslinked, water-absorbing polymer with a mixture comprising an aqueous solvent and at least one salt of a transition metal; and
B) irradiating the polymer treated according to Step A with UV radiation.

DETAILED DESCRIPTION

"Absorbent structure" refers to any three dimensional structure, useful to absorb and retain bodily liquids, such as urine or blood.

"Diapers for babies and infants", "feminine hygiene articles" and "incontinence articles" refers to devices that absorb and retain bodily liquids (such as blood and urine), and more specifically, refers to devices that are placed against or in proximity to the body of the wearer to absorb and contain the various exudates discharged from the body. "Diaper for babies and infants" refers to an absorbent article generally worn about the lower torso. The term "diaper for babies and infants" comprise taped diapers, which are applied to the wearer using tapes or other suitable closing means. The term "diaper for babies and infants" also comprises pull-on pants, and pull-on training pants, which are pant-like diapers having fixed sides and leg openings. Such pant-like diapers are placed in position on the wearer by inserting the wearer's legs into the leg openings and sliding the pant-like diaper into position about the wearer's lower torso.

"Feminine hygiene articles" refers to sanitary napkins, panty liners, interlabial devices and tampons.

"Incontinence articles" refers to refers to an absorbent article generally worn about the lower torso of adults. The term "incontinence articles" comprise taped diapers, which are applied to the adult wearer using tapes or other suitable closing means. The term "incontinence articles" also comprises pull-on pants for adults, and pull-on training pants for adults, which are pant-like diapers for adults having fixed sides and leg openings. Such pant-like diapers are placed in position on the adult wearer by inserting the wearer's legs into the leg openings and sliding the pant-like diaper into position about the wearer's lower torso. The term "incontinence articles" also comprises adult incontinent briefs.

"Disposable" is used herein to describe articles that are generally not intended to be laundered or otherwise restored or reused (i.e., they are intended to be discarded after a single use and, may be, to be recycled, composted or otherwise disposed of in an environmentally compatible manner).

The diapers for babies and infants, feminine hygiene articles and incontinence articles of the present disclosure may be disposable.

The absorbent structure as disclosed may be any absorbent structure, used to absorb and retain bodily liquids, such as urine or blood.

The absorbent structure typically comprises the water-swellable material herein and a structuring material, such as a core wrap or wrapping material, support layer for the water-swellable material or structuring agent such as described below.

The absorbent structure is typically, or forms typically part of a diaper for babies and infants, a feminine hygiene article and/or an incontinence article.

The absorbent structure as disclosed is typically that part of a diaper for babies and infants, a feminine hygiene article and/or an incontinence article which serves to store and/or acquire bodily fluids, the absorbent structure may be the storage layer, or the acquisition layer, or both, either as two or more layers or as unitary structure.

The absorbent structure may be a structure that consists of the water-swellable material and that is then shaped into the required three-dimensional structure, or it may comprise additional components, such as those used in the art for absorbent structures.

The absorbent structure may also comprise one or more support or wrapping materials, such as foams, films, woven webs and/or nonwoven webs, as known in the art, such as spunbond, meltblown and/or carded nonwovens. One material that may be used is a so-called SMS material, comprising a spunbonded, a melt-blown and a further spunbonded layer. Other materials that may be used are permanently hydrophilic nonwovens, and in particular nonwovens with durably hydrophilic coatings. Further, materials comprising an SMMS-structure may be used. The top layer and the bottom layer may be provided from two or more separate sheets of materials or they may be alternatively provided from a unitary sheet of material Non-woven materials may be provided from synthetic fibers, such as PE, PET and PP. As the polymers used for nonwoven production are inherently hydrophobic, they may be coated with hydrophilic coatings, e.g. coated with nanoparticles, as known in the art.

The absorbent structure may also comprise a structuring agent or matrix agent, such as absorbent fibrous material, such as airfelt fibers, and/or adhesive, which each may serve to immobilize the water-swellable material.

Because the water-swellable material herein has an excellent permeability, even when swollen, there is no need for large amounts of structuring agents, such as absorbent fibrous material (airfelt), as normally used in the art.

Thus, a relatively low amount or no absorbent fibrous (cellulose) material is used in the absorbent structure. Thus, it may be preferred that said structure herein comprises large amounts of the water-swellable material herein and only very little or no absorbent (cellulose) fibers, e.g., less than 20% by weight of the water-swellable material, or even less than 10% by weight of the water-swellable material, or even less than 5% by weight.

Absorbent structures disclosed herein comprise a layer of a substrate material such as the core-wrap materials described herein, and thereon a water-swellable material layer, optionally as a discontinuous layer, and thereon a layer of an adhesive or thermoplastic material or a (fibrous) thermoplastic adhesive material, which is laid down onto the layer of water-swellable material. It may be that the thermoplastic or adhesive layer is then in direct contact with the water-swellable material, but also partially in direct contact with the substrate layer, where the substrate layer is not covered by the absorbent polymeric material. This imparts an essentially three-dimensional structure to the (fibrous) layer of thermoplastic or adhesive material, which in itself is essentially a two-dimensional structure of relatively small thickness (in z-direction), as compared to the extension in x- and y-direction.

Thereby, the thermoplastic or adhesive material provides cavities to hold the water-swellable material and thereby immobilizes this material. In a further aspect, the thermoplastic or adhesive material bonds to the substrate and thus affixes the water-swellable material to the substrate.

In this embodiment, it may be preferred that no absorbent fibrous material is present in the absorbent structure.

The thermoplastic composition may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic composition may be a hot melt adhesive comprising at least one thermoplastic polymer in combination with other thermoplastic diluents such as tackifying resins, plasticizers and additives such as antioxidants.

The thermoplastic polymer has typically a molecular weight (Mw) of more than 10,000 and a glass transition temperature (Tg) usually below room temperature. As disclosed, a wide variety of thermoplastic polymers are suitable for use. Such thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alphaolefins.

The resin has typically a Mw below 5,000 and a Tg usually above room temperature, typical concentrations of the resin in a hot melt are in the range of 30-60%. The plasticizer has a low Mw of typically less than 1,000 and a Tg below room temperature, a typical concentration is 0-15%.

The adhesive may be present in the form of fibres throughout the core, i.e. the adhesive is fiberized.

The fibres may have an average thickness of 1-50 micrometer and an average length of 5 mm to 50 cm.

The absorbent structure, in particular when no or little absorbent fibres are present, as described above, has a density greater than about 0.4 g/cm$^3$. The density may be greater than about 0.5 g/cm$^3$, or greater than about 0.6 g/cm$^3$.

Absorbent structures can for example be made as follows:
a) providing a substrate material that can serve as a wrapping material;
b) depositing the water-swellable material herein onto a first surface of the substrate material, in a pattern comprising at least one zone which is substantially free of water-swellable material, and the pattern comprising at least one zone comprising water-swellable material, such that openings are formed between the separate zones with water-swellable material;
c) depositing a thermoplastic material onto the first surface of the substrate material and the water-swellable material, such that portions of the thermoplastic material are in direct contact with the first surface of the substrate and portions of the thermoplastic material are in direct contact with the water-swellable material;
d) and then typically closing the above by folding the substrate material over, or by placing another substrate matter over the above.

The absorbent structure may comprise an acquisition layer and a storage layer, which may have the same dimensions, however it may be preferred that the acquisition layer is laterally centered on the storage layer with the same lateral width but a shorter longitudinal length than storage layer. The acquisition layer may also be narrower than the storage layer while remaining centered thereon. Said another way, the acquisition layer suitably has an area ratio with respect to storage layer of 1.0, but the area ratio may be less than 1.0, e.g. less than about 0.75, or less than about 0.50.

For absorbent structures for diapers for babies and infants, feminine hygiene articles and/or an incontinence articles designed for absorption of urine, it may be preferred that the acquisition layer is longitudinally shorter than the storage layer and positioned such that more than 50% of its longitudinal length is forward of transverse axis of the absorbent structure or of the diaper for babies and infants, feminine hygiene article and/or incontinence article herein. This positioning is desirable so as to place acquisition layer under the point where urine is most likely to first contact the absorbent structure or the diaper for babies and infants, the feminine hygiene article and/or the incontinence article.

Also, the absorbent core, or the acquisition layer and/or storage layer thereof, may comprise an uneven distribution of water-swellable material basis weight in one or both of the machine and cross directions. Such uneven basis weight distribution may be advantageously applied in order to provide extra, predetermined, localized absorbent capacity to the absorbent structure or diaper for babies and infants, feminine hygiene article and/or incontinence article.

The absorbent structure as disclosed may be, or may be part of a diaper for babies and infants, a feminine hygiene article and/or an incontinence article, typically it may be the absorbent core of such an article, or the storage layer and/or acquisition layer of such an article.

Diapers for babies and infants, feminine hygiene articles and/or incontinence articles as disclosed herein may have a topsheet and a backsheet, which each have a front region, back region and crotch region, positioned therein between. The absorbent structure as disclosed is typically positioned in between the topsheet and backsheet. The backsheets may be vapour pervious but liquid impervious. The topsheet materials may be at least partially hydrophilic and may be apertured. It may be that the topsheet comprises a skin care composition, e.g. a lotion.

These diapers for babies and infants, feminine hygiene articles and/or incontinence articles typically comprise a liquid impervious (and in some embodiments, air or water vapour pervious) backsheet, a fluid pervious topsheet joined to, or otherwise associated with the backsheet. Such articles are well known in the art and fully disclosed in various documents mentioned throughout the description.

Because the water-swellable material herein has a very high absorbency capacity, it is possible to use only low levels of this material in the diapers for babies and infants, feminine hygiene articles and/or incontinence articles herein. These thin diapers for babies and infants, feminine hygiene articles and/or incontinence articles, such as adult and infant diapers, training pants, sanitary napkins may comprise an absorbent structure as disclosed, such that the articles may have an average caliper (thickness) in the crotch region of less than 1.0 cm, less than 0.7 cm, less than 0.5 cm, or even less than 0.3 cm (for this purpose alone, the crotch region being defined as the central zone of the product, when laid out flat and stretched, having a dimension of 20% of the length of the article and 50% of the width of the article).

Because the water-swellable material herein have a very good permeability, there is no need to have large amounts of traditional structuring agents presents, such as absorbent fibres, such as airfelt, and the may thus be omitted or only used in very small quantities, as described above. This further helps to reduce the thickness of the absorbent structure, or diapers for babies and infants, feminine hygiene articles and/ or incontinence articles herein.

The diapers for babies and infants, feminine hygiene articles and/or incontinence articles disclosed herein may achieve a relatively narrow crotch width, which increases the wearing comfort. Articles disclosed herein may achieves a crotch width of less than 100 mm, 90 mm, 80 mm, 70 mm, 60 mm or even less than 50 mm, as measured along a transversal line with is positioned at equal distance to the front edge and the rear edge of the article. Hence, an absorbent structure may have a crotch width as measured along a transversal line with is positioned at equal distance to the front edge and the rear edge of the core which is of less than 100 mm, 90 mm, 80 mm, 70 mm, 60 mm or even less than 50 mm. It has been found that for most diapers for babies and infants, feminine hygiene articles and/or incontinence articles the liquid discharge occurs predominately in the front half.

Diapers for babies and infants, as well as a incontinence article herein, may have a front waist band and a back waist band, whereby the front waist band and back waist band each have a first end portion and a second end portion and a middle portion located between the end portions, and whereby preferably the end portions comprise each a fastening system, to fasten the front waist band to the rear waist band or whereby the end portions are connected to one another, and whereby the middle portion of the back waist band and/or the back region of the backsheet and/or the crotch region of the backsheet comprises a landing member, the landing member comprising second engaging elements selected from loops, hooks, slots, slits, buttons, magnets. Hooks, adhesive or cohesive second engaging elements may be used. The engaging elements on the diaper may be provided with a means to ensure they are only engage able at certain moments, for example, they may be covered by a removable tab, which is removed when the engaging elements are to be engaged and may be re-closed when engagement is no longer needed, as described above.

The diapers for babies and infants, feminine hygiene articles and/or incontinence articles herein may have one or more sets of leg elastics and/or barrier leg cuffs, as known in the art.

The topsheet may have an opening with an elastication means along the length thereof, where through waste material can pass into a void space above the absorbent structure, and which ensures it is isolated in this void space, away from the wearer's skin.

Water-Absorbing Polymers

Processes for producing non-surface-crosslinked water-absorbing polymers, also referred to hereinafter as base polymer, are known.

Water-absorbing polymers are obtained, for example, by polymerizing a monomer solution comprising
  a) at least one ethylenically unsaturated monomer bearing acid groups,
  b) at least one crosslinker,
  c) if appropriate one or more ethylenically and/or allylically unsaturated monomers copolymerizable with the monomer a) and
  d) if appropriate one or more water-soluble polymers, on to which the monomers a), b) and, if appropriate, c) can be grafted at least partly.

Suitable monomers a) are, for example, ethylenically unsaturated carboxylic acids, such as acrylic acid, methacrylic acid, maleic acid, fumaric acid and itaconic acid, or derivatives thereof, such as acrylamide, methacrylamide, acrylic esters and methacrylic esters. Monomers that may be useful include acrylic acid and methacrylic acid.

The monomers a), especially acrylic acid, comprise up to 0.025% by weight of a hydroquinone monoether. A preferred hydroquinone monoethers that may be used is hydroquinone monomethyl ether (MEHQ) and/or tocopherols.

Tocopherol is understood to mean compounds of the following formula

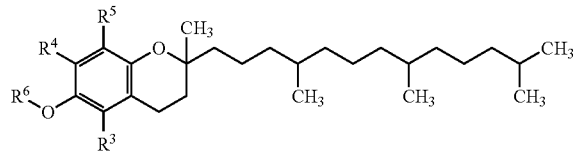

where $R^3$ is hydrogen or methyl, $R^4$ is hydrogen or methyl, $R^5$ is hydrogen or methyl and $R^6$ is hydrogen or an acyl radical having from 1 to 20 carbon atoms.

Preferred radicals for $R^6$ that may be useful include acetyl, ascorbyl, succinyl, nicotinyl and other physiologically compatible carboxylic acids. The carboxylic acids may be mono-, di- or tricarboxylic acids.

Alpha-tocopherol where $R^3=R^4=R^5=$methyl, especially racemic alpha-tocopherol, may be useful. $R^6$ may be hydrogen or acetyl. RRR-alpha-tocopherol may be especially useful.

In certain embodiments, the monomer solution may comprise at most 130 ppm by weight, or at most 70 ppm by weight, and at least 10 ppm by weight, at least 30 ppm by weight, or about 50 ppm by weight, of hydroquinone monoether, based in each case on acrylic acid, acrylic acid salts also being counted as acrylic acid. For example, the monomer solution can be prepared by using an acrylic acid having an appropriate content of hydroquinone monoether.

The crosslinkers b) are compounds having at least two polymerizable groups which can be polymerized by free-radical means into the polymer network. Suitable crosslinkers b) are, for example ethylene glycol dimethacrylate, diethylene glycol diacrylate, allyl methacrylate, trimethylolpropane triacrylate, triallylamine tetraallyloxyethane, as described in EP 530 438 A1, di- and triacrylates, as described in EP 547 847 A1, EP 559 476 A1, EP 632 068 A1, WO 93/21 237 A1, WO 03/104 299 A1, WO 03/104 300 A1, WO 03/104 301 A1 and DE 103 31 450 A1, mixed acrylates, which, as well as acrylate groups, comprise further ethylenically unsaturated groups, as described in DE 103 31 456 A1 and WO 04/013 064 A2, or crosslinker mixtures, as described, for example, in DE 195 43 368 A1, DE 196 46 484 A1, WO 90/15 830 A1 and WO 02/032 962 A2.

Suitable crosslinkers b) are especially N,N'-methylenebisacrylamide and N,N'-methylenebismethacrylamide, esters of unsaturated mono or polycarboxylic acids of polyols, such as diacrylate or triacrylate, for example butanediol diacrylate, butanediol dimethacrylate, ethylene glycol diacrylate or ethylene glycol dimethacrylate, and also trimethylolpropane triacrylate and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid, and vinylphosphonic acid derivatives, as described, for example, in EP 343 427 A2. Further suitable crosslinkers b) are pentaerythritol diallyl ether, pentaerythritol triallyl ether and pentaerythritol tetraallyl ether, polyethylene glycol diallyl ether, ethylene glycol diallyl ether, glyceryl diallyl ether and glyceryl triallyl ether, polyallyl ethers based on sorbitol, and ethoxylated variants thereof. In the process disclosed, it is possible to use di(meth) acrylates of polyethylene glycols, where the polyethylene glycol used has a molecular weight between 300 and 1000.

Particularly advantageous crosslinkers b) are, however, di- and triacrylates of 3- to 15-tuply ethoxylated glycerol, of 3- to 15-tuply ethoxylated trimethylolpropane, of 3- to 15-tuply ethoxylated trimethylolethane, especially di- and triacrylates of 2- to 6-tuply ethoxylated glycerol or trimethylolpropane, of 3-tuply propoxylated glycerol or trimethylolpropane, and of 3-tuply mixed ethoxylated or propoxylated glycerol or trimethylolpropane, of 15-tuply ethoxylated glycerol or trimethylolpropane, and of 40-tuply ethoxylated glycerol, trimethylol ethane or trimethylol propane.

In certain embodiments, crosslinkers b) are the polyethoxylated and/or propoxylated glycerols which have been esterified with acrylic acid or methacrylic acid to give di- or triacrylates, as described, for example, in WO 03/104 301 A1. Particularly advantageous are di- and/or triacrylates of 3- to 10-tuply ethoxylated glycerol. In certain embodiments di- or triacrylates of 1- to 5-tuply ethoxylated and/or propoxylated glycerol may be used. In certain embodiments, triacrylates of 3- to 5-tuply ethoxylated and/or propoxylated glycerol may be used. These feature particularly low residual contents (typically below 10 ppm by weight) in the water-absorbing polymers, and the aqueous extracts of the water-absorbing polymers prepared with them have an almost unchanged surface tension (typically at least 0.068 N/m) compared to water at the same temperature.

Ethylenically unsaturated monomers c) copolymerizable with the monomers a), are, for example, acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

The water-soluble polymers d) used may be polyvinyl alcohol, polyvinylpyrrolidone, starch, starch derivatives, polyglycols, polymers which have been formed in a formal sense completely or partly from vinylamine monomers, such as partly or fully hydrolyzed polyvinylamide (so-called "polyvinylamine") or polyacrylic acids, including polyvinyl alcohol and starch.

The polymerization is, if appropriate, performed in the presence of customary polymerization regulators. Suitable polymerization regulators are, for example, thio compounds, such as thioglycolic acid, mercapto alcohols, e.g. 2-mercaptoethanol, mercaptopropanol and mercaptobutanol, dodecyl mercaptan, formic acid, ammonia and amines, e.g. ethanolamine, diethanolamine, triethanolamine, triethylamine, morpholine and piperidine.

The monomers (a), (b) and, if appropriate (c) are, if appropriate, in the presence of the water-soluble polymers d), (co) polymerized with one another in from 20 to 80% by weight, from 20 to 50% by weight, or from 30 to 45% by weight, aqueous solution in the presence of polymerization initiators. The polymerization initiators used may be all compounds which decompose to free radicals under the polymerization conditions, for example peroxides, hydroperoxides, hydrogen peroxide, persulfates, azo compounds and the so-called redox initiators. The use of water-soluble initiators may be useful. In some cases, it is advantageous to use mixtures of different polymerization initiators, for example, mixtures of hydrogen peroxide and sodium peroxodisulfate or potassium peroxodisulfate. Mixtures of hydrogen peroxide and sodium peroxodisulfate can be used in any desired ratio. Suitable organic peroxides are, for example, acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, tert-butyl per-3,5,5-trimethylhexanoate and tert-amyl perneodecanoate. Further suitable polymerization initiators are azo initiators, for example 2,2'-azobis-(2-amidinopropane) dihydrochloride, 2,2'-azobis-(N,N-dimethylene)isobutyramidine dihydrochloride, 2-(carbamoylazo)isobutyronitrile and 4,4'-azobis(4-cyanovaleric acid). The polymerization initiators mentioned are used in customary amounts, for example in amounts of from 0.01 to 5 mol %, or from 0.1 to 2 mol %, based on the monomers to be polymerized.

The redox initiators comprise, as the oxidizing component at least one of the above-specified per compounds and a reducing component, for example ascorbic acid, glucose, sorbose, ammonium hydrogensulfite, sulfite, thiosulfate, hyposulfite, pyrosulfite or sulfide, or alkali metal hydrogen sulfite, sulfite, thiosulfate, hyposulfite, pyrosulfite or sulfide, metal salts such as iron(II) ions or silver ions, or sodium hydroxymethylsulfoxylate. It may be desirable to use, as the reducing component of the redox initiator, ascorbic acid or sodium pyrosulfite. Based on the amount of monomers used in the polymerization, from $1 \cdot 10^{-5}$ to 1 mol % of the reducing component of the redox initiator and from $1 \cdot 10^{-5}$ to 5 mol % of the oxidizing component are used. Instead of the oxidizing component or in addition, it is also possible to use one or more water-soluble azo initiators.

In certain embodiments, it may be desirable to use a redox initiator consisting of hydrogen peroxide, sodium peroxodisulfate and ascorbic acid. For example, these components are used in the concentrations of $1 \cdot 10^{-2}$ mol % of hydrogen peroxide, 0.084 mol % of sodium peroxodisulfate and $2.5 \cdot 10^{-3}$ mol % of ascorbic acid, based on the monomers.

The aqueous monomer solution may comprise the initiator in dissolved or dispersed form. The initiators may, however, also be supplied to the polymerization reactor separately from the monomer solution.

For optimal action, the polymerization inhibitors require dissolved oxygen. Therefore, the polymerization inhibitors can be freed of dissolved oxygen before the polymerization by inertization, i.e. blowing an inert gas through, e.g., nitrogen. This is done by means of inert gas which can be introduced in co-current, counter-current or intermediate angles of entry. Good mixing can be achieved, for example with nozzles, static or dynamic mixers or bubble columns. The oxygen content of the monomer solution may be lowered before the polymerization to less than 1 ppm by weight, or to less than 0.5 ppm by weight. The monomer solution is, if appropriate, conducted through the reactor with an inert gas stream.

The preparation of a suitable base polymer and further suitable hydrophilic ethylenically unsaturated monomers a) are described, for example in DE 199 41 423 A1, EP 686 650 A1, WO 01/45 758 A1 and WO 03/104 300 A1.

Non-surface-crosslinked water-absorbing polymers (base polymers) are typically obtained by polymerizing an aqueous monomer solution and, if appropriate, a subsequent comminution of the hydrogel. Suitable preparation processes are described in the literature. base polymers are obtained, for example, by:

gel polymerization in a batch process or tubular reactor and subsequent comminution in a meat grinder, extruder or kneader, as described, for example, in EP 445 619 A2 and DE 19 846 413 A1;

polymerization in a kneader, continuous comminution being effected by means of, for example counter-rotating kneader shafts, as described in WO 01/38 402 A1;

polymerization on a belt and subsequent comminution in a meat grinder, extruder or kneader as described in EP 955 086 A2, DE 38 25 366 A1 or U.S. Pat. No. 6,241,928;

emulsion polymerization, which already affords bead polymers of relatively narrow gel size distribution, as described in EP 457 660 A1;

droplet polymerization as described in WO2006/079631 A1;

in-situ polymerization of a fabric layer, which, usually in continuous operation, has been sprayed beforehand with aqueous monomer solution and then subjected to a photo-polymerization, as described in WO 02/94 328 A2, WO 02/94 329 A1).

With regard to details of the process procedure, reference is hereby made explicitly to the documents cited. The reaction may be carried out in a kneader or on a belt reactor.

The preparation process for water-absorbing polymers which may be preferred for economic reasons and is therefore currently customary is that of continuous gel polymerization. First, a monomer solution is prepared by adding the neutralizing agent, optional comonomers and/or further assistants to the acrylic acid solution at different times and/or spatially separately, and then transferring the mixture into the reactor, or actually initially charging it in the reactor. As the last addition, the initiator system is metered in at the start of the polymerization. In the continuous polymerization process which follows, the reaction proceeds to give the polymer gel (i.e. the polymer swollen to a gel in the solvent of the polymerization—typically water), which in the case of a kneader polymerization, is already comminuted in advance. The polymer gel is subsequently dried and, if required, also crushed, ground and screened, and transferred to further surface treatment.

The acid groups of the resulting hydrogels are typically partly neutralized, generally to an extent of at least 25 mol %, to an extent of at least 27 mol % or to an extent of at least 40 mol %, and generally at most 85 mol %, at most 80 mol %, or at most 75 mol %, for which the customary neutralizing agents can be used, including alkali metal hydroxides, alkali metal oxides, alkali metal carbonates or alkali metal hydrogencarbonates, and mixtures thereof. Instead of alkali metal salts, it is also possible to use ammonium salts. Sodium and potassium may be used as alkali metals, but in certain embodiments, particular preference is given to sodium hydroxide, sodium carbonate or sodium hydrogencarbonate and mixtures thereof. Typically, the neutralization is achieved by mixing in the neutralizing agent as an aqueous solution or as a solid. For example, sodium hydroxide with water content significantly below 50% by weight may be present as a waxy material with a melting point above 23° C. In this case, metered addition as piece material or a melt at elevated temperature is possible.

The neutralization can be carried out after the polymerization, at the hydrogel stage. However, it is also possible to carry out the neutralization to the desired degree of neutralization entirely or partly before the polymerization. In the case of partial neutralization before the polymerization, generally at least 10 mol %, or at least 15 mol %, and generally at most 40 mol %, at most 30 mol %, or at most 25 mol % of the acid groups in the monomers used are neutralized before the polymerization, by adding a portion of the neutralizing agent actually to the monomer solution. The desired final degree of neutralization in this case is not established until toward the end of or after the polymerization, preferably at the hydrogel stage, before it is dried. The monomer solution is neutralized by mixing in the neutralizing agent. The hydrogel can be mechanically comminuted in the course of neutralization, for example by means of a meat grinder or comparable apparatus for comminuting gellike materials, in which case the neutralizing agent is sprayed on, scattered over or poured on and then mixed in carefully. To this end, the resulting gel material can be subjected to meat grinding several times more for homogenization. The monomer solution may be adjusted to the desired final degree of neutralization by adding the neutralizing agent before polymerization.

The gels obtained from the polymerization are, if appropriate, kept for a certain time, for example at least 30 minutes, at least 60 minutes or at least 90 minutes, and generally at most 12 hours, at most 8 hours or at most 6 hours, at a temperature of generally at least 50° C. or at least 70° C. and generally at most 130° C. or at most 100° C., which often allows their properties to be improved further.

The neutralized hydrogel is then dried with a belt drier or roll drier until the residual moisture content is below 15% by weight, or below 10% by weight, the water content being determined by the EDANA (European Disposables and Nonwovens Association) recommended test method No. 430.2-02 "Moisture Content". The dry water-absorbing polymer consequently comprises up to 15% by weight of moisture, or at most 10% by weight. What is crucial for the classification as "dry" is especially sufficient free flow for handling as a powder (for instance for pneumatic delivery, transferring, screening or other process steps from solid-state process technology). If appropriate, for drying, it is also possible to use a fluidized bed drier or a heated ploughshare mixer. In order to obtain particularly colorless products, it is advantageous in the course of drying of this gel to ensure that the evaporating water is rapidly transported away. To this end, the drier temperature has to be optimized, the air supply and removal have to be controlled, and sufficient venting has to be ensured in each case. By its nature, the higher the solids content of the gel, the simpler the drying and the more colorless the product. The solvent content in the polymerization is therefore adjusted such that the solids content of the gel before the drying is therefore generally at least 20% by weight, at least 25% by weight or at least 30% by weight, and generally at most 90% by weight, at most 85% by weight or at most 80% by weight. It is particularly advantageous to vent the drier with nitrogen or another non-oxidizing inert gas. If appropriate though, it is also possible simply to lower only the partial pressure of the oxygen during the drying, in order to prevent oxidative yellowing processes. In general, however, even sufficient venting and removal of the water vapor lead to a product which is still acceptable. With regard to color and product quality, a very short drying time is generally advantageous.

The dried hydrogel (which is no longer a gel—even though it is still referred to as such—but rather a dry polymer with superabsorbent properties) may be ground and screened. For the grinding, roll mills, pin mills, hammer mills, cutting mills or vibratory mills are typically used, and, for the screening, gravity screening machines, gyratory screening machines, tumbling screening machines or drum screening machines. The particle size of the screened dry hydrogel (base polymer) is below 1000 µm, below 900 µm, or below 850 µm, and preferably above 80 µm, above 90 µm, or above 100 µm.

In certain embodiments, preference is given to hydrogels which have a particle size distribution (sieve cuts a), b) and c)) in which
  a) less than 10% by weight, less than 5% by weight, or less than 1% by weight, of the polymer particles have a particle size of more than 710 µm,
  b) at least 80% by weight, at least 90% by weight, or at least 95% by weight, of the polymer particles have a particle size of from 150 to 710 µm and
  c) at least 50% by weight, at least 70% by weight, or at least 90% by weight, of the polymer particles have a particle size of from 300 to 600 µm.

In certain embodiments, preference is also given to hydrogels which have a particle size distribution (sieve cuts a), b) and c)) in which
  a) less than 10% by weight, less than 5% by weight, or less than 1% by weight, of the polymer particles have a particle size of more than 850 µm,
  b) at least 80% by weight, at least 90% by weight, or at least 95% by weight, of the polymer particles have a particle size of from 150 to 850 µm and
  c) at least 1% by weight, at least 10% by weight, or at least 20% by weight, of the polymer particles have a particle size of less than 300 µm.

The particle size distribution is determined by the EDANA (European Disposables and Nonwovens Association) recommended test method No. 420.2-02 "Particle size distribution".

In step A) the particulate, non-surface-crosslinked, water-absorbing polymer (base polymer) is treated with a mixture comprising an aqueous solvent and at least one salt of a transition metal. The mixture is typically liquid. The salt is present dissolved or suspended in the solvent. In the context of the present disclosure, a transition metal is understood to mean elements of the periodic table whose atoms have an only partly filled d shell. Transition metals that may be used include the elements of the 4th period with atomic numbers 23-29, of the 5th period with atomic numbers 41 to 47 and of the 6th period with atomic numbers 57 to 79.

In certain embodiments, preference is given to salts with transition metal cations whose red/ox potential relative to hydrogen is $\geq +0.5$ V. The values reported here for the red/ox potential are based on a 1 normal aqueous solution at 25° C.

In certain embodiments, preference is given to inorganic salts with transition metal cations, especially those whose red/ox potential relative to hydrogen is $\geq +0.5$ V. In certain embodiments, preference is given to inorganic salts with polyvalent transition metal cations, especially those whose red/ox potential relative to hydrogen is $\geq +0.5$ V.

Transition metal cations whose red/ox potential relative to hydrogen is $\geq +0.5$ V, are disclosed, for example, in "Lange's Handbook of Chemistry" (16th edition) 2005 McGraw-Hill, chapter 1.21. In certain embodiments, preferred transition metal cations include $Ag^+$, $Fe^{3+}$, $Cr^{3+}$ and $Ce^{4+}$. The metal cations may be used either alone or in a mixture thereof. In addition, salts of transition metals which have a plurality of different cations, known as mixed salts, are suitable. In this connection, especially those salts which are mixtures of transition metals and ammonium, for example ammonium cerium (IV) nitrate are suitable.

It is also possible to generate the transition metal cations whose red/ox potential relative to hydrogen is $\geq 0.5$ V, directly on the surface of the base polymer particles. In this embodiment, the transition metal cation is used in its reduced form and is oxidized on the surface with the per-compounds specified below or hydrogen peroxide. In certain embodiments, preferred transition metal cations in reduced form include $Ag^0$, $Fe^{2+}$, $Cr^{2+}$ and $Ce^{3+}$.

Among the transition metal cations, it may be desirable to use salts which have a sufficient solubility in the aqueous solvent. Sufficient solubility should be understood to mean that they exhibit, in the aqueous solvent at a temperature of 20° C. and 1 bar, a solubility of $\geq 10$ g/l. Particularly suitable metal salts are those with weakly complexing anions, for example iodide, bromide, chloride, nitrate and sulfate, hydrogensulfate, carbonate, hydrogencarbonate, phosphate, hydrogenphosphate, dihydrogenphosphate and carboxylates, such as formate, acetate, propionate, oxalate and lactate. Especially suitable as salts of transition metals are chlorides, nitrates and sulfates. In certain embodiments, it may be preferred to use salts of transition metals including ammonium cerium(IV) nitrate, iron(III) sulfate, iron(III) chloride, chromium(III) sulfate and silver nitrate.

Aqueous solvents are understood to mean water and mixtures of water with water-miscible solvents. Water-miscible solvents are understood to mean those which are miscible with water up to an amount of 30% by weight based on the mixture of water and solvent at 25° C. and 1 bar. These include alcohols such as methanol, ethanol, n-propanol, isopropanol, n-butanol, sec-butanol, tert-butanol, 2-methyl-1-propanol, propanediols, butanediols, glycerol and methoxyethanol, glycols such as ethylene glycol, diethylene glycol and polyethylene glycols or polypropylene glycols having a mean molecular weight $M_w$ of $\leqq 1000$, ethers and glycol ethers such as dioxane, tetrahydrofuran and polyethylene glycol ether, ketones such as acetone, butanone and cyclohexanone or carboxylic esters, such as ethyl acetate. In certain embodiments, particular preference is given to water and water/alcohol mixtures for example water/2-propanol, water/1,2-propanediol and water/1,3-propanediol.

Based on the non-surface-crosslinked, water-absorbing polymer (base polymer) at least 0.0001% by weight, from 0.01 to 5% by weight, or from 0.1 to 1% by weight, of the salt of a transition metal is used.

The base polymer is treated with the salt of a transition metal, for example, by spraying a mixture comprising the aqueous solvent and the salt of a transition metal, which may preferably be a solution of the salt of the transition metal in the aqueous solvent, on to the base polymer. The spraying-on of the mixture may preferably be carried out in mixers with moving mixing tools, such as screw mixers, paddle mixers, disk mixers, ploughshare mixers and paddle mixers, mixers with moving vessels, such as drum mixers, tumbler mixers and cone mixers and mixers by gas-induced mixing, such as mixing silos, jet mixers and fluidized bed mixers. In certain embodiments, preference is given to vertical mixers, and in certain other embodiments, preference is given to ploughshare mixers and paddle mixers. Suitable and known mixers are, for example, Lödige®, Bepex®, Nauta®, Processall® and Schugi® mixers. In certain embodiments, preference is given to using high-speed mixers for example of the Schugi-Flexomix® or Turbolizer® type. In certain embodiments, preference is given to spraying on a mixture, especially a solution, of the salt of the transition metal in a fluidized bed mixer.

In addition, in step A) the particulate, non-surface-crosslinked, water-absorbing polymer (base polymer) can additionally be treated with at least one compound selected from the group comprising water-soluble per compounds, ethylenically unsaturated carboxylic acids and/or salts thereof, free-radical crosslinkers and deagglomeration agents.

The per-compound may be either an organic or an inorganic per compound. In certain embodiments, preference is given to inorganic per compounds such as perborates, persulfates and peroxides. In certain embodiments, preference is given to these inorganic per compounds with monovalent cations such as sodium, potassium and/or ammonium. In certain embodiments, preference is given to persulfates.

Based on the non-surface-crosslinked, water-absorbing polymer (base polymer) from 0.01 to 5% by weight, or from 0.1 to 1% by weight, of the per compound is used.

This treatment of the base polymer with the water-soluble per compound can be effected with the mixture of per compound, the salt of the transition metal and the aqueous solvent or separately, such that there is a kind of mixing only on the base polymer. In certain embodiments, preference is given to effecting the addition separately.

Suitable ethylenically unsaturated carboxylic acids are the carboxylic acids listed above under monomers a). Examples include acrylic acid, methacrylic acid, maleic acid, fumaric acid and itaconic acid. Useful monomers may include acrylic acid and methacrylic acid. In certain embodiments, preference is given to acrylic acid.

The ethylenically unsaturated carboxylic acids may be used either in their acid form or as salts or mixtures of the two. In certain embodiments, preference is given to alkali metal salts, including sodium salts.

In certain embodiments, preference is given to using carboxylic acids having a degree of neutralization of from 0 to 80, i.e. the acid or a mixture of salt and acid is used in which up to 80 mol % of the acid is present in the form of salt.

Based on the non-surface-crosslinked, water-absorbing polymer (base polymer) from 0.01 to 5% by weight, or from 0.1 to 1% by weight, of the ethylenically unsaturated carboxylic acid and/or salt thereof is used, this being the total amount of carboxylic acid and salt thereof.

This treatment of the base polymer with the ethylenically unsaturated carboxylic acid and/or salt thereof can be effected with the mixture of carboxylic acid and/or salt thereof, the aqueous solvent and the salt of the transition metal, or with the individual substances, such that there is a kind of mixing only on the base polymer. The ethylenically unsaturated carboxylic acid and/or salt thereof may be a constituent of the mixture of aqueous solvent and salt of the transition metal.

Suitable free-radical crosslinkers are the crosslinkers having at least two free-radically polymerizable groups listed above under b). Suitable crosslinkers b) are, for example, ethylene glycol dimethacrylate, diethylene glycol diacrylate, allyl methacrylate, trimethylolpropane triacrylate, triallylamine, tetraallyloxyethane and mixed acrylates which, as well as acrylate groups, comprise further ethylenically unsaturated groups.

Suitable crosslinkers b) are especially N,N'-methylenebisacrylamide and N,N'-methylenebismethacrylamide, esters of unsaturated mono or polycarboxylic acids of polyols such as diacrylate or triacrylate and allyl compounds. In certain embodiments, preferred crosslinkers b) are the polyethoxylated and/or propoxylated glycerols which have been esterified with acrylic acid or methacrylic acid to give di- or triacrylates, and the polyethylene glycols which have been esterified with acrylic acid or methacrylic acid to give diacrylates.

Based on the non-surface-crosslinked, water-absorbing polymer (base polymer) from 0.001 to 0.5% by weight, or from 0.01 to 0.1% by weight of the crosslinker is used.

This treatment of the base polymer with the free-radical crosslinker can be effected with the mixture of crosslinker, the aqueous solvent and the transition metal salt, or with the individual substances, such that there is a kind of mixing only on the base polymer. The crosslinker may be a constituent of the mixture of aqueous solvent and the salt of the transition metal.

In certain embodiments, in step A) the base polymer is additionally treated with at least one ethylenically unsaturated carboxylic acid and/or salt thereof and/or a free-radical crosslinker.

In certain embodiments, the base polymer, in step A) is additionally treated with at least one free-radical crosslinker.

In certain embodiments, in step A), the base polymer is additionally treated with at least one deagglomeration agent.

Deagglomeration agents in the context of the present disclosure are fine substances in powdery or fibrous form which are inert with respect to the preparation conditions of the components and of the mixtures and may be of organic or inorganic nature. Examples of such additives are: fine silicon dioxide, fumed silicas, precipitated silicas in hydrophilic or hydrophobic polymorphs, zeolites, titanium dioxide, zirconium dioxide, zinc oxide, talc, bentonites of any type, cellulose, silicates of any type, guar flour, tara flour, carob flour, all kinds of starches, clays, barium sulfate, calcium sulfate.

Likewise deagglomeration agents in the context of the present disclosure are liquid substances which are inert with respect to the preparation conditions of the components and of the mixtures and may be of organic or inorganic nature. Examples of such additives are: silicones, for example in the form of oils and oil emulsions in water, waxes, for example natural and synthetic paraffins with and without functional groups, metal soaps, for example metal salts of fatty acids, such as calcium stearate, lead stearate, magnesium stearate, aluminum stearate and zinc stearate, polymers, for example polyvinyl alcohol, polyesters and polyolefins and nonionic surfactants, and polyoxyethylene alkyl ethers as described in WO 2006/062258 as assistants.

Based on the non-surface-crosslinked, water-absorbing polymer (base polymer) from 0.001 to 10% by weight, or 0.01 to 5% by weight of the deagglomeration agent is used.

This treatment of the base polymer with the deagglomeration agent can be effected with the mixture of deagglomeration agent, the aqueous solvent and the transition metal salt, or with the individual substances, such that there is a kind of mixing only on the base polymer. In certain embodiments, preference is given to adding the deagglomeration agent separately.

When the content of aqueous solvent in the treated base polymer falls below a value of 3% by weight after the treatment step A), it is advisable to moisten the treated base polymer. This can occur especially in one of the preferred variants, in which a fluidized bed mixer is selected, or in a variant in a heated mixer. The moistening can be accomplished with one of the abovementioned aqueous solvents, including water. The moistening, including spraying, is effected up to a solvent content of from >3 to 20% by weight, or from 5 to 15% by weight, based on the moistened base polymer.

The irradiation is effected by customary processes known to those skilled in the art. UV radiation is understood by the person skilled in the art to mean radiation of wavelengths from 1 to 400 nm, or from 150 to 350 nm. Suitable for irradiation are, for example, conventional UV radiators such as high-pressure, medium-pressure and low-pressure mercury radiators, and also fluorescent tubes, pulse radiators, lasers, metal halide radiators, xenon radiators and halogen radiators or excimer radiators. The radiation dose typically sufficient for crosslinking is within the range from 10 to 5000 mJ/cm$^2$. The irradiation time is from 0.1 seconds to 60 minutes, from 0.5 seconds to 30 minutes, or from 1 second to 15 minutes.

The polymer particles can be irradiated either in suspension with a liquid or in a gas or gas mixture. When the irradiation is effected in suspension with a liquid, the suspension should be transparent to UV radiation, i.e. not extinguish more than 10% of the 400 nm wavelength. Suitable liquids mentioned by way of example are heptane or cyclohexane. In certain embodiments, preference is given to irradiating the polymer particles in a gaseous environment which may comprise water vapor. In certain embodiments, preferred gases or gas mixtures are air, water vapor and/or inert gas, such as nitrogen, carbon dioxide, noble gases or combustion gases, and also mixtures thereof. The gas mixture may comprise water vapor. In certain embodiments, preference is given to performing the irradiation of the polymer particles in an atmosphere composed of water vapor-containing air with a relative air humidity of from 20 to 100%.

In the embodiment in which the polymer particles are irradiated in a gas/gas mixture, the pressure in the gas space is adjusted to a value in the range from 0.001 to 10 bar, from 0.1 to 3 bar, from 0.5 to 1.5 bar, or to standard pressure.

The temperature selected for the irradiation mixture is a value in the range from 0° C. to 250° C., from 20° C. to 200° C., from 40° C. to 180° C., or from 60° C. to 140° C. According to the energy input, there may be heating of the irradiation mixture. If appropriate, it may be advisable to cool or to heat it to the desired value.

In a further embodiment as disclosed, in addition to the UV irradiation, treatment by IR radiation can also be effected. The IR irradiation can be effected before, in parallel to and/or after the UV irradiation. IR radiation is understood by the person skilled in the art to mean radiation of wavelengths from 780 nm to 1 mm.

After the irradiation in process step B), the treated polymer, in on of the variants (process step C), is dried. In certain embodiments, preference is given to drying down to a water content of $\leq$20% by weight, of $\leq$5% by weight, or of $\leq$3% by weight. This drying is effected, for example, by thermal treatment at a temperature of at least 40° C. and at most 250° C., within a temperature range from 60 to 200° C., or from 80° C. to 180° C.

The mean residence time (i.e. the average residence time of the individual water-absorbing polymer particles) of the polymer obtained from step C) in the drier is generally at least 1 minute, at least 3 minutes, or at least 5 minutes, and generally at most 6 hours, at most 2 hours, or at most 1 hour.

The thermal treatment is effected, for example, in a heated mixer ("drier") such as staged driers, rotary tube driers or heatable screws, including in contact driers. In certain embodiments, preference is given to the use of driers in which the product is agitated, i.e. heated mixers, paddle driers, and/or disk driers. Suitable driers are, for example, Bepex® driers and Nara® driers. Moreover, it is also possible to use convection driers such as belt driers and fluidized bed driers. However, the drying can also be effected convectively in the mixer itself, for example by combining the heating of the jacket with the supply of a preheated gas, such as air.

Thereafter, it may be advantageous to cool the inventive water-absorbing material. The cooling can be effected continuously or discontinuously; conveniently, the product, for this purpose, is conveyed continuously into a cooler connected downstream of the drier. To this end, any apparatus known for the removal of heat from powders can be used, especially any apparatus mentioned above as a drying apparatus, provided that it is not supplied with a heating medium but rather with a cooling medium, for instance with cooling water, such that no heat is introduced into the water-absorbing polymers via the walls and, according to the construction, also via the mixing units or other heat exchange surfaces, but rather is removed therefrom. In certain embodiments, preference is given to the use of coolers in which the product is agitated, i.e. cooled mixers, for example paddle coolers, disk coolers or paddle coolers, for instance in Nara® or Bepex® coolers. The water-absorbing material can also be cooled in a fluidized bed by blowing in a cooled gas such as cold air. The conditions of the cooling are adjusted such that a water-absorbing material with the temperature desired for the further processing is obtained. Typically, a mean residence time in the cooler of generally at least 1 minute, at least 3 minutes, or at least 5 minutes, and generally at most 6 hours, 2 hours, or at most 1 hour is established, and the cooling performance is such that the resulting product has a temperature of generally at least 0° C., at least 10° C., or at least 20° C., and generally at most 100° C., at most 80° C., or at most 60° C.

Optionally, a further modification of the water-absorbing material can also be effected by adding a deagglomeration agent. Suitable deagglomeration agents are those mentioned above.

If appropriate, the water-absorbing material is provided with further customary additives and assistants which influence storage or handling properties. Examples thereof are colorings, opaque additives in order to improve the visibility of swollen gel, which is desirable in some applications, additives for improving the flow behavior of the powder or the like. Often, dedusting agents or dust binding agents are added to the water-absorbing material. dedusting agents or dust binding agents are known; for example polyether glycols such as polyethylene glycol having a molecular weight of from 400 to 20 000 g/mol, polyols such as glycerol, sorbitol, neopentyl glycol or trimethylolpropane, which are optionally also 7- to 20-tuply ethoxylated, are used. A finite water content of the water-absorbing material can also be established by adding water, if desired.

The solids, additives and assistants can each be added in separate process steps; however, the most convenient method is usually to add them to the water-absorbing material in the cooler, for instance by spraying on a solution or adding them in fine solid form or in liquid form.

The water-absorbing material is, if appropriate, typically ground and/or screened. Grinding is typically not required here, but the screening-off of agglomerates formed or fines is usually appropriate to establish the desired particle size distribution of the product. Agglomerates and fines are either discarded or are recycled into the process in a known manner and at a suitable point; agglomerates after comminution. The particle size of the water-absorbing material is at most 1000 μm, at most 900 μm, or at most 850 μm, and at least 80 μm, at least 90 μm, or at least 100 μm. Typical sieve cuts are for example from 106 to 850 μm or from 150 to 710 μm.

The inventive water-absorbing material exhibits a good absorption under pressure (AUP) and can be produced within a short processing time and without thermal stress. In the process disclosed, by virtue of the irradiation, a crosslinking reaction likewise takes place at the surface of the base polymer. It is assumed that it is not a crosslinking by virtue of the condensation reactions via the acid radicals, but rather a free-radical reaction probably takes place.

Test Methods

Absorption Under Pressure ("AUP", "Absorption Under Pressure"):

The AAP (0.3 psi) is determined by the EDANA (European Disposables and Nonwovens Association, Avenue Eugène Plasky 157, 1030 Brussels, Belgium) recommended test method No. 442.2-02, obtainable therefrom.

EXAMPLES

A) Preparation of the Base Polymer

A Lödige VT 5R-MK ploughshare kneader (capacity 5 liters) was initially charged with a reaction mixture composed of 183 g of water, 239 g of acrylic acid and 2148 g of a 37.3% by weight sodium acrylate solution (100 mol % neutralized) and also 2.8 g of 3-tuply ethoxylated glyceryl triacrylate, and inertized by sparging with nitrogen for 20 minutes. The reaction mixture was cooled externally such that the subsequent addition of initiator was effected at approx. 20° C. With stirring, the initiators (2.39 g of sodium persulfate (dissolved in 13.53 g of water), 0.05 g of ascorbic acid (dissolved in 10.18 g of water)) and 0.14 g of 30% by weight hydrogen peroxide (dissolved in 1.28 g of water) were added to the kneader in rapid succession. The reaction set in rapidly and, on attainment of an internal temperature of 30° C., the jacket of the kneader was heated with heat carrier medium at 80° C. in order to conduct the reaction to the end as adiabatically as possible. On attainment of the maximum temperature, the gel formed was cooled down in the kneader to below 50° C. by means of cooling liquid (−12° C.) and then discharged.

The gel was distributed on two metal sheets with a wire base and dried in a forced-air drying cabinet at 160° C. Subsequently, a Retsch laboratory ultracentrifugal mill was used to comminute it to a particle size of from 150 to 600 μm.

The base polymer GP-A thus prepared had an AAP (0.3 psi) of 10.9 g/g.

Example 1

A 20 ml beaker was charged with 3 g of acetone, 7 g of demineralized water and 2.5 g of ammonium cerium(IV) nitrate which were stirred for 10 min. 2 g of the resulting solution were sucked in with a syringe (capacity 10 ml with steel cannula).

20 g of the base polymer GP-A prepared according to Example A) were introduced into a Waring laboratory blender. The blender was set to level I and the 2 g of solution was sprayed on to the mixing base polymer all at once via the syringe. The sprayed base polymer BP-1 was thus obtained. The sprayed base polymer BP-1, immediately after the spraying, was spread out very uniformly over the area of a Petri dish (diameter 12 cm). A Höhnle UV radiator (UVA-Spot 400, power 400 watts) was then placed immediately over the filled Petri dish at a distance of 5 cm and the polymer sample was irradiated for 1 min. To this route the surface-crosslinked polymer OP-2 was obtained.

The resulting product (designated as OP-1) exhibited good performance properties. In addition, the product OP-1 was dried in a forced-air drying cabinet at 105° C. for 1 hour and, in this way the dry material TG-1 was obtained.

The measurement of the AAP (0.3 psi) gave a value of 16.1 g/g for the sprayed base polymer BP-1, a value of 21.4 g/g for the irradiated polymer OP-1, and a value of 23.2 g/g for the dry material TG-1.

Example 2

Non-Inventive

A 20 ml beaker was charged with 3 g of acetone, 7 g of demineralized water and 0.5 g of oxazolidinone which were stirred for 10 min. 2 g of the resulting solution were sucked in with a syringe (capacity 10 ml with steel cannula).

20 g of the base polymer GP-A were introduced into a Waring laboratory blender. The blender was set to level I and the 2 g of solution were sprayed on to the mixing base polymer all at once via the syringe. The sprayed base polymer BP-2 was thus obtained. The sprayed base polymer BP-2, immediately after the spraying, was spread out very uniformly over the area of a Petri dish (diameter 12 cm). The polymer sample was then placed into a forced-air drying cabinet preheated to 200° C. and removed again after 1 min. In this way, the surface-crosslinked polymer OP-2 was obtained.

The measurement of the AAP (0.3 psi) gave a value of 9.4 g/g for the sprayed base polymer BP-2, and a value of 10.7 g/g for the surface-crosslinked polymer OP-2.

Example 3

Non-Inventive

A 20 ml beaker was charged with 3 g of acetone, 7 g of demineralized water and 2.5 g of a 30% by weight aqueous hydrogen peroxide solution which were stirred for 10 min. 2 g of the resulting solution were sucked in with a syringe (capacity 10 ml with steel cannula).

20 g of the base polymer GP-A were introduced into a Waring laboratory blender. The blender was set to level I and the 2 g of solution were sprayed on to the mixing base polymer all at once via the syringe. The sprayed base polymer BP-3 was thus obtained.

The sprayed base polymer BP-3, immediately after the spraying, was spread out very uniformly over the area of a Petri dish (diameter 12 cm). A Höhnle UV radiator (UVA-Spot 400, power 400 watts) was then placed immediately above the filled Petri dish at a distance of 5 cm and the polymer sample was irradiated for 1 min. In this way, the irradiated polymer OP-3 was obtained.

The measurement of the AAP (0.3 psi) gave a value of 10.4 g/g for the sprayed base polymer BP-3, and a value of 8.0 g/g for the irradiated polymer OP-3.

Example 4

A 20 ml beaker was charged with 3 g of acetone, 7 g of demineralized water and 2.5 g of iron(III) chloride and 2.5 g of acrylic acid, which were stirred for 10 min. 2 g of the resulting solution were sucked in with a syringe (capacity 10 ml with steel cannula).

20 g of the base polymer GP-A prepared according to Example A) were introduced into a Waring laboratory blender. The blender was set to level I and the 2 g of solution were sprayed on to the mixing base polymer all at once by means of the syringe. The sprayed base polymer BP-4 was thus obtained.

The sprayed base polymer BP-4, immediately after the spraying, was spread out very uniformly over the area of a Petri dish (diameter 12 cm). A Höhnle UV radiator (UVA-Spot 400, power 400 watts) was then placed immediately over the filled Petri dish at a distance of 5 cm and the polymer sample was irradiated for 1 min. The resulting product is designated as OP-4. In addition, the product OP-4 was dried in a forced-air drying cabinet at 105° C. for 1 hour and, in this way, the dry material TG-4 was obtained.

The measurement of the AAP (0.3 psi) gave a value of 14.7 g/g for the sprayed base polymer BP-4, a value of 22.9 g/g for the irradiated polymer OP-4, and a value of 26.3 g/g for the dry material TG-4.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent structure for use in a diaper for babies and infants, a feminine hygiene article, and/or an incontinence article, the absorbent structure comprising:
   a water-absorbing material obtained by a process comprising the steps of:
   A) treating a particulate, non-surface-crosslinked, water-absorbing polymer with a mixture comprising an aqueous solvent and at least one salt of a transition metal; and
   B) irradiating the polymer treated according to Step A with UV radiation.

2. The absorbent structure of claim 1, wherein the salt of a transition metal has a cation whose red/ox potential relative to hydrogen is greater than or equal to about +0.5 V.

3. The absorbent structure of claim 1, wherein the salt of a transition metal is an inorganic salt.

4. The absorbent structure of claim 1, wherein the salt of the transition metal has a solubility in aqueous solvents of greater than or equal to about 10 g/l.

5. The absorbent structure of claim 1, wherein from about 0.1 to about 5% by weight of the salt of a transition metal, based on the non-surfacecrosslinked water-absorbing polymer, is applied.

6. The absorbent structure of claim 1, wherein a mixture comprising the aqueous solvent and the salt of a transition metal is sprayed onto the particulate, non-surface-crosslinked, water-absorbing polymer in a fluidized bed.

7. The absorbent structure of claim 1, wherein in Step A the non-surface-crosslinked water-absorbing polymer is treated with at least one ethylenically unsaturated carboxylic acid and/or alkali metal salt thereof and/or a free-radical crosslinker.

8. The absorbent structure of claim 1, wherein in Step A, the non-surface-crosslinked water-absorbing polymer is treated with at least one free-radical crosslinker.

9. The absorbent structure of claim 1, wherein at least one deagglomeration agent is added in Step A.

10. An absorbent structure for use in a diaper for babies and infants, a feminine hygiene article, and/or an incontinence article, the absorbent structure comprising:

a water-absorbing material obtainable by a process comprising the steps of:
A) treating a particulate, non-surface-crosslinked, water-absorbing polymer with a mixture comprising an aqueous solvent and at least one salt of a transition metal;
B) irradiating the polymer treated according to Step A with UV radiation; and
C) drying the material obtained according to Step B.

11. A process for producing an absorbent structure for use in a diaper for babies and infants, a feminine hygiene article, and/or an incontinence article, the process comprising the steps of:

A) treating a particulate, non-surface-crosslinked, water-absorbing polymer with a mixture comprising an aqueous solvent and at least one salt of a polyvalent transition metal;
B) irradiating the polymer treated according to Step A with UV radiation; and
C) subsequently drying the material obtained according to Step B.

* * * * *